US011338002B2

(12) United States Patent
Biffi (10) Patent No.: US 11,338,002 B2
(45) Date of Patent: May 24, 2022

(54) USE FOR TREATMENT OF CLOSTRIDIUM DIFFICILE INFECTIONS

(71) Applicant: LAC2BIOME S.R.L, Milan (IT)

(72) Inventor: Andrea Biffi, Urgnano (IT)

(73) Assignee: LAC2BIOME S.R.L., Milan (IT)

( * ) Notice: Subject to any disclaimer, the term of this patent is extended or adjusted under 35 U.S.C. 154(b) by 29 days.

(21) Appl. No.: 16/642,337

(22) PCT Filed: Sep. 12, 2018

(86) PCT No.: PCT/IB2018/056956
§ 371 (c)(1),
(2) Date: Feb. 26, 2020

(87) PCT Pub. No.: WO2019/053604
PCT Pub. Date: Mar. 21, 2019

(65) Prior Publication Data
US 2020/0306323 A1    Oct. 1, 2020

(30) Foreign Application Priority Data

Sep. 12, 2017    (IT) .................. 102017000101704

(51) Int. Cl.
*A61K 35/747*    (2015.01)
*A61P 31/04*    (2006.01)
*A61K 9/00*    (2006.01)

(52) U.S. Cl.
CPC .......... *A61K 35/747* (2013.01); *A61K 9/0031* (2013.01); *A61K 9/0053* (2013.01); *A61P 31/04* (2018.01)

(58) Field of Classification Search
CPC .............. A61K 39/09; A61K 2039/572; A61K 39/025; C07K 16/1267; C07K 14/24; C07K 16/1228; A61P 31/04
See application file for complete search history.

(56) References Cited

U.S. PATENT DOCUMENTS

2016/0348155 A1* 12/2016 Guglielmetti .......... C12Q 1/689

FOREIGN PATENT DOCUMENTS

WO    WO 2005/123100 A1    12/2005

OTHER PUBLICATIONS

Balzaretti et al., (Front Microbiol 2015. 6:952. Published online Sep. 15, 2015). (Year: 2015).*
D'Inca et al., (Digestive Diseases and Sciences 56(4): 1178-87. Apr. 2011). (Year: 2011).*
Leuzzi et al., (Human Vaccines and Immunotherapeutic. vol. 10. Issue6. 2014) (Year: 2014).*
Larry K. Kociolek & Dale N. Gerding (Nature Reviews Gastroenterology & Hepatology 13, 150-160. 2016) (Year: 2016).*
(Continued)

*Primary Examiner* — Jana A Hines
(74) *Attorney, Agent, or Firm* — James S. Keddie; Bozicevic, Field & Francis LLP (57) ABSTRACT

The present invention relates to the use of specific strains of *Lactobacillus paracasei* or of a composition comprising said strains for the prevention and/or treatment of a physiopathological condition related to/associated with *Clostridium difficile* infection, preferably intestinal infections, or so-called CD-associated disease (CDAD) or CD infection (CDI).

16 Claims, 3 Drawing Sheets

A

B (56) References Cited

OTHER PUBLICATIONS

Balzaretti et al., "The vaginal isolate Lactobacillus paracasei LPC-S01 (DSM 26760) is suitable for oral administration", Frontiers in Microbiology, 2015, vol. 6, Article 952.

European Food Safety Authority (EFSA), "Scientific Opinion on the substantiation of health claims related to Lactobacillus casei DG CNCM I-1572 and decreasing potentially pathogenic gastrointestinal microorganisms (ID 2949, 3061, further assessment) pursuant to Article 13(1) of Regulation (EC) No. 1924/2006", EFSA Journal, 2012, 10(6): 2723.

Gao et al., "Dose—Response Efficacy of a Proprietary Probiotic Formula of Lactobacillus acidophilus CL1285 and Lactobacillus casei LBC80R for Antibiotic-Associated Diarrhea and Clostridium difficile—Associated Diarrhea Prophylaxis in Adult Patients", The American Journal of Gastroenterology, 2010, 105: 1636-1641.

\* cited by examiner

USE FOR TREATMENT OF CLOSTRIDIUM DIFFICILE INFECTIONS

CROSS-REFERENCE TO RELATED APPLICATIONS

This application is a § 371 national phase of International Application No. PCT/IB2018/056956, filed on Sep. 12, 2018, which claims the benefit of Italian Application No. 102017000101704, filed on Sep. 12, 2017, which applications are incorporated by reference herein.

The present invention relates to the use of specific strains of *Lactobacillus paracasei* or of a composition comprising said strains for the prevention and/or treatment of a physiopathological condition related to/associated with *Clostridium difficile* infection, preferably intestinal infections, or so-called CD-associated disease (CDAD) or CD infection (CDI).

PRIOR ART

*Clostridium difficile* is a gram-positive, anaerobic, spore-forming, rod-shaped bacterium widely disseminated in nature, both in the subsoil and in the intestinal tract of pets.

Contamination by this microorganism also occurs through the fecal-oral route; in particular, the spores ingested survive the acid barrier of the stomach and germinate in the colon.

In humans, *Clostridium difficile* may be found in about 3% of healthy adults as a constituent of intestinal saprophytic flora and, in more substantial percentages, in infants under one year of age (15-70%).

*Clostridium difficile* generally does not cause any disorder. However, under certain conditions, it may cause diarrhea of variable intensity and, in certain cases, it may be associated with fever as well as a major general impairment of a person's state of health from a physical, psychological and social standpoint. In fact, the diarrhea is often accompanied by other major symptoms, such as: nausea, vomiting, general malaise, pain, abdominal distension and dehydration.

In the clinical realm, *Clostridium difficile* is known as being mainly responsible for a severe form of colitis, defined as pseudomembranous colitis, characterized by more or less extensive necrosis, prevalently affecting the rectum and sigmoid colon, and accompanied by often profuse diarrhea.

A cause for concern in this regard are in particular several strains of *Clostridium difficile*, defined as enterotoxigenic as they are capable of producing enterotoxin A and/or cytotoxin B. These toxins are internalized by the intestinal mucosa, bringing about the cell death of enterocytes.

The spectrum of histological lesions varies from a type I form, characterized by sporadic epithelial necrosis associated with an inflammatory infiltrate inside the lumen of the colon, to a type III form, characterized by widespread epithelial necrosis and ulcerations covered by greyish pseudomembranes (hence the term pseudomembranous colitis), made up of mucin, neutrophils, fibrin and cellular debris.

The severity of *Clostridium difficile* intestinal infection is variable. The symptoms can in fact range from mild to profuse diarrhea (up to 10 liters of serous discharges per day), with toxic megacolon, intestinal perforation, hypokalemia, intestinal hemorrhaging, and sepsis. The diarrhea can be accompanied by fever, nausea, anorexia, general malaise, pain, abdominal distension and dehydration. The diarrhea can be associated with mucus, blood and fever. Infants are often asymptomatic carriers. In fact, though on the one hand colonization appears to be favored by the immaturity of intestinal bacterial flora, on the other hand the lack of pathological evolution is due to the incapacity of the toxin to bind to the receptors of enterocytes, which are also still immature.

The infection often manifests itself following aggressive antibiotic therapies and very commonly spreads in hospital environments. Diarrhea is a common side effect of antibiotic therapies, but once the drug is suspended at the end of treatment the disorder normally resolves. However, in the case of *Clostridium*, the diarrhea, accompanied by the other symptoms, shows no sign of decreasing or improving.

Among the risk factors for *Clostridium difficile* infection we may mention:
  Use of antibiotics, especially broad-spectrum ones (i.e. the ones that are capable of eliminating various types of bacteria), also for an extended period, or associations of different antibiotics to cure antibiotic-resistant infections;
  Need for hospitalization or stays in other treatment facilities;
  Digestive system surgery;
  Abdominal surgery involving the intestine;
  Stays in a kindergarten, nursery school or rest home;
  Colon problems, e.g. irritable bowel syndrome or colorectal cancer;
  Kidney problems;
  Weakened immune system (due to diabetes or drugs);
  Intake of proton pump inhibitors or other drugs capable of reducing gastric acidity, which normally serves as protection against infections;
  Previous *Clostridium difficile* infections;
  Age above 65 years.

Treatment of the infection in any case requires the use of antibiotics, albeit ones that particularly target this specific bacterium.

As noted earlier, the majority of *Clostridium difficile* infections occur in settings such as, for example, hospitals and nursing homes, in which many individuals take antibiotics and are in close contact with one another. The lethality of severe *Clostridium difficile* infection is considerable, so much so as to make the adoption of prophylactic measures indispensable in order to stem the spread of the disease in hospital environments.

In recent years, various cases have been successfully treated with the fecal transplantation method.

Recourse to probiotics has proven effective in the prevention/treatment of most types of diarrhea, comprising that induced precisely by *Clostridium difficile*, through the competitive inhibition of the pathogens, stabilization of resident microbiota and attenuation of the increase in intestinal permeability associated, for example, with rotavirus infections.

In the light of the foregoing, there is a strongly felt need for new and/or alternative therapeutic solutions which may alleviate the symptoms associated therewith and/or cure the physiopathological conditions related to/associated with *Clostridium difficile* infections, preferably intestinal infections.

The Applicant has found the use of probiotics based on bacteria and/or yeast and/or other micro-organisms as a solution to the above-described needs. In particular, the present solution proposes the use of bacteria belonging to the genus *Lactobacillus* and/or *Bifidobacterium*, preferably the bacterial species *Lactobacillus paracasei*.

In fact, as a result of the use of probiotics, as described in detail below, an inhibition of *Clostridium difficile* is observed, evident above all from in vitro displacement tests.

DESCRIPTION OF THE FIGURES

The present invention will be described in detail below, also with the aid of the following figures and with examples that are not intended to have any limiting character.

In particular.

DETAILED DESCRIPTION

In this context, the definition of "probiotic" is the one formulated by a group of experts jointly convened in 2001 by the FAO and the WHO: "Live micro-organisms which when administered in adequate amounts confer a health benefit on the host". In particular, in Italy, the Ministry of Health has defined probiotics as "micro-organisms which demonstrate to be able, once ingested in sufficient amounts, to exert functions that are beneficial for the body", substantially echoing the definition of the two above-mentioned organizations.

*Clostridium difficile* (hereinafter CD) is a bacterium clinically responsible for various types of infections or diseases/conditions associated therewith known as CD-associated disease (CDAD) or CD infection (CDI) and which can be characterized by different degrees of severity.

In fact, the infection can manifest itself as mild diarrhea, but can also result in pseudomembranous colitis, toxic megacolon and intestinal perforation. The severe clinical manifestations, with which above all a risk of mortality is associated, are more frequent if the infection is sustained by new more virulent bacterial strains.

CD infection is typically of nosocomial origin and also manifests itself quite frequently with an epidemic character.

A first aspect of the present invention relates to the bacterial strain *L. casei* DG® and/or the bacterial strain *Lactobacillus paracasei* LPC-S01 or a composition comprising said strain(s) for use in the prevention and/or in the treatment of a physiopathological condition related to/associated with *Clostridium difficile* infection, preferably intestinal infections, or so-called CD-associated disease (CDAD) or CD infection (CDI).

Said disease associated with *Clostridium difficile* is preferably selected from: pseudomembranous enterocolitis, pseudomembranous colitis, colitis without pseudomembranes, fulminant colitis, colitis with toxic megacolon and intestinal perforation, colitis associated with antibiotics, diarrhea associated with antibiotics and diarrhea associated with *C. difficile* infection.

Both strains were isolated and deposited by SOFAR S.p.A. The bacterial strain *L. casei* DG® (*Lactobacillus paracasei* CNCM I-1572) was deposited with the National Collection of Cultures of Micro-organisms of the Pasteur Institute of Paris with the deposit number CNCM I-1572. The strain initially had the designation *Lactobacillus casei* DG sub.*casei*. The bacterial strain *Lactobacillus paracasei* LPC-S01 was deposited with the DSMZ with the following accession number: DSM 26760.

The strains of *Clostridium difficile* to which reference is made in this context are preferably the ones defined as enterotoxigenic, i.e. capable of producing enterotoxins/cytotoxins, such as, for example cytotoxin B and/or enterotoxin A. In a broader context, *C. difficile* strains that do not produce toxins and are not pathogenic and new emerging ones, which are hypervirulent, resistant to antibiotics and hyper-producers of spores, will also be considered.

The administration of the bacterial strain *L. casei* DG® and/or of the bacterial strain *Lactobacillus paracasei* LPC-S01 or of said composition is preferably effective for alleviating and/or treating and/or curing the symptoms associated with said infections/CDAD/CDI and/or the histological lesions caused by CD infection or CD-associated disease.

In fact the infections/associated diseases caused by CD can be characterized by different degrees of severity. The infection can manifest itself as mild diarrhea, but can also end up causing abdominal situations such as, for example, protein-losing enteropathy and recurrent diarrhea, and extra-intestinal situations such as, for example, bacteremia and splenic abscess. The severe clinical manifestations, such as dehydration, hypokalemia, septic shock, pseudomembranous colitis, toxic megacolon and intestinal perforation, which are above all associated with a risk of mortality, are more frequent if the infection is sustained by new more virulent bacterial strains.

Therefore, according to a preferred aspect of the present invention, said symptoms associated with said infections/CDAD/CDI are selected from: diarrhea, dehydration, pseudomembranous colitis, enteropathies, toxic megacolon, intestinal perforation, sepsis, intestinal hemorrhaging and hypokalemia.

The histological lesions are preferably type I and/or type III.

According to a preferred aspect of the present invention, said composition comprises further micro-organisms, preferably bacteria, preferably probiotic bacteria, and/or yeasts and/or fungi.

Said bacteria preferably belong to a genus selected from: *Lactobacillus, Bifidobacterium, Bacillus, Propionibacterium, Streptococcus, Lactococcus, Aerococcus, Enterococcus* and combinations thereof; more preferably, said bacteria belong to the genus *Lactobacillus* and/or *Bifidobacterium*.

According to a further preferred aspect of the invention, the bacteria of the genus *Lactobacillus* belong to at least one of the following species: *Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermenturn, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus sakei, Lactobacillus salivarius* and *Lactobacillus sanfranciscensis*.

According to a further preferred embodiment, said bacteria belonging to the genus *Lactobacillus* are not the strain *Lactobacillus acidophilus* CL1285, and/or *Lactobacillus casei* LBC8OR and/or *Lactobacillus rhamnosus* CLR2.

According to a further embodiment of the invention, said bacterial strain *L. casei* DG® and/or said bacterial strain *Lactobacillus paracasei* LPC-S01 or said composition comprising said strain(s) further comprise (are used in combination with) bacteria belonging to the genus *Lactobacillus* which are not the strain *Lactobacillus acidophilus* CL1285, and/or *Lactobacillus casei* LBC8OR and/or *Lactobacillus rhamnosus* CLR2.

According to a further preferred aspect of the invention, the bacteria of the genus *Bifidobacterium* belong to at least one species selected from: *B. animalis, B. bifidum, B. breve, B. infantis, B. longum, B. adolescentis, B. catenulatum, B. angulaturn, B. asteroides, B. bourn, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum B. thermophilum* and *B. tsurumiense*; more preferably selected from: *Bacillus clausii, Bacillus subtilis, Bacillus coagulans, Bacillus megaterium Bacillus halodurans, Bacillus thuringiensis, Bacillus insolitus* and *Bacillus marinus*.

According to a further preferred aspect of the invention, the bacteria of the genus *Propionibacterium* belong to at least one species selected from: *P. shermanii, P. acnes, P. australiense, P. avidum, P. cyclohexanicum, P. freudenreichii, P. granulosum, P. jensenii, P. microaerophilum, P. propionicum* and *P. thoenii*.

According to a further preferred aspect of the invention, the bacteria of the genus *Streptococcus* belong to at least one species selected from: *Streptococcus thermophilus, Streptococcus salivarius, Streptococcus agalactiae, Streptococcus anginosus, Streptococcus bovis, Streptococcus canis, Streptococcus constellatus, Streptococcus downei, Streptococcus dysgalactiae, Streptococcus equinus, Streptococcus ferns, Streptococcus infantarius, Streptococcus iniae, Streptococcus intermedius, Streptococcus milleri, Streptococcus mitis, Streptococcus mutans, Streptococcus orails, Streptococcus orisratti, Streptococcus parasanguinis, Streptococcus peroris, Streptococcus pneumoniae, Streptococcus pseudopneumoniae, Streptococcus pyogenes, Streptococcus ratti, Streptococcus tigurinus, Streptococcus sanguinis, Streptococcus sobrinus, Streptococcus suis, Streptococcus uberis, Streptococcus vestibularis, Streptococcus viridans* and *Streptococcus zooepidemicus*.

According to a further preferred aspect of the invention, the bacteria of the genus *Lactococcus* belong to at least one species selected from: *L. chungangensis, L. formosensis, L. fujiensis, L. garvieae, L. lactis, L. piscium, L. plantarum, L. raffinolactis* and *L. taiwanensis*.

According to a further preferred aspect of the invention, the bacteria of the genus Aerococcus belong to at least one species selected from: *A. urinae, A. sanguinicola, A. christensenii, A. suis, A. urinaeequi* and *A. urinaehominis*.

According to a further preferred aspect of the invention, the bacteria of the genus *Enterococcus* belong to at least one species selected from: *Enterococcus avium, Enterococcus durans, Enterococcus faecalis, Enterococcus faecium, Enterococcus gallinarum, Enterococcus haemoperoxidus, Enterococcus hirae, Enterococcus malodoratus, Enterococcus moraviensis, Enterococcus mundtii, Enterococcus pseudoaviaum, Enterococcus raffinosus* and *Enterococcus solitarius*.

According to a further preferred aspect of the invention, the yeasts belong to the genus *Saccharomyces*, more preferably the species *Saccharomyces cerevisiae* and/or *Saccharomyces boulardii*.

Said bacterial strain *L. casei* DG® and/or said bacterial strain *Lactobacillus paracasei* LPC-S01 and/or said further micro-organisms are preferably live. In the latter case, the resulting composition is also definable as a probiotic.

Alternatively, said bacterial strain *L. casei* DG® and/or said bacterial strain *Lactobacillus paracasei* LPC-S01 and/or said further micro-organisms are dead or tyndallized.

In a further embodiment, said bacterial strain *L. casei* DG® and/or said bacterial strain *Lactobacillus paracasei* LPC-S01 and/or said further micro-organisms are in the form of a lysate and/or extract.

In the latter case, the resulting composition is also definable as a paraprobiotic.

Alternatively, said bacterial strain *L. casei* DG® and/or said bacterial strain *Lactobacillus paracasei* LPC-S01 and/or said further micro-organisms can be present as an individual component thereof, or several components, present in the bacterial wall as an exopolysaccharide.

In a further embodiment of the invention, the composition further comprises the metabolic bioproducts generated by said bacterial strain *L. casei* DG® and/or by said bacterial strain *Lactobacillus paracasei* LPC-S01 and/or by said further micro-organisms defined as postbiotics and/or any other bacteria-derived product.

Therefore, the composition as described above is also definable as a probiotic or a paraprobiotic or a postbiotic, known or assumed, or a component of the bacterial wall.

In general, said micro-organisms further comprised in the composition of the present invention are single micro-organisms or combinations of any microbial species specified in the CPS list of the EFSA.

Said bacterial strain *L. casei* DG® and/or said bacterial strain *Lactobacillus paracasei* LPC-S01 and/or said further micro-organisms are capable of surviving gastrointestinal transit and therefore of reaching the colon alive.

Said bacterial strain *L. casei* OG® and/or said bacterial strain *Lactobacillus paracasei* LPC-S01 and/or said further micro-organisms, if present, are administered in an amount ranging from 1 billion to 300 billion (or more according to need), more preferably 50-250 billion, even more preferably 75-150 billion cells, preferably bacterial cells, per administration. In the event of application via enema and/or fecal transplantation, said bacterial strain *L. casei* OG® and/or said bacterial strain *Lactobacillus paracasei* LPC-S01 and/or said further micro-organisms, if present, are administered in an amount ranging from 100 to 300 billion, more preferably from 150 to 200 billion cells, preferably bacterial cells/probiotics/composition per administration/application.

According to a preferred aspect, said bacterial strain *L. casei* DG® and/or said bacterial strain *Lactobacillus paracasei* LPC-S01 and/or said further micro-organisms, if present, preferably bacteria, are taken at least once-twice daily.

Every route of administration is envisaged in the present invention. The administration of said bacterial strain *L. casei* OG® and/or of said bacterial strain *Lactobacillus paracasei* LPC-S01 and/or of said composition as described above is preferably oral, more preferably in the form of pills, capsules, tablets, granular powder, hard-shelled capsules, orally dissolving granules, sachets, lozenges or drinkable vials.

Alternatively, the administration of said bacterial strain *L. casei* DG® and/or of said bacterial strain *Lactobacillus paracasei* LPC-S01 and/or of said composition as described above, is in liquid form, preferably a syrup or beverage.

Alternatively, the administration of said bacterial strain *L. casei* DO® and/or of said bacterial strain *Lactobacillus paracasei* LPC-S01 and/or of said composition takes place by addition to a food, preferably yogurt, cheese or fruit juice.

A further aspect of the present invention relates to probiotics, preferably comprising bacteria belonging to a genus selected from: *Lactobacillus, Bifidobacterium, Bacillus, Propionibacterium, Streptococcus, Lactococcus, Aerococcus, Enterococcus* and combinations thereof, or a composition comprising said probiotics, for use in the prevention and/or in the treatment of a physiopathological condition related to/associated with *Clostridium difficile* infection, preferably intestinal infections, or so-called CD-associated disease (GOAD) or CD infection (CDI), wherein said probiotic or composition is formulated in such a way as to exert action topically, preferably by rectal administration, preferably as an enema, preferably by fecal microbiota transplantation.

The bacteria are preferably the bacterial strain *L. casei* DG® and/or the bacterial strain *Lactobacillus paracasei* LPC-S01 and/or said composition as described above.

The formulations of probiotics or the composition as described above further comprise excipients generally accepted for the production of probiotic and/or pharmaceutical products.

According to a preferred aspect of the invention, the formulations of probiotics or the composition further comprise anti-caking agents, preferably silicon dioxide and/or magnesium stearate.

According to a preferred aspect of the invention, the composition further comprises coating agents, preferably gelatin.

In a further embodiment of the invention, the formulations of probiotics or the composition further comprise vitamins, trace elements, preferably zinc or selenium, enzymes and/or prebiotic substances, preferably fructo-oligosaccharides (FOS), galacto-oligosaccharides (GOS), inulin, guar gum or combinations thereof.

According to a preferred aspect of the present invention, the formulations of probiotics or the composition may be associated or combined with further therapeutic approaches, preferably of a pharmacological or socio-behavioral type, preferably a diet and/or a healthy lifestyle.

EXAMPLE

The pathogens used in the following examples were obtained from the ATCC American Type Culture Collection and belong to the following strain: *Clostridium difficile* ATCC 43255-VPI 10463.

The strains tested were the following:
1) *L. casei* DG® (*Lactobacillus paracasei* CNCM I-1572),
2) *Lactobacillus paracasei* LPC-S01; and
3) a combination (mixture) in a 1:1 ratio of *L. casei* DG® and *L. paracasei* LPC-S01.
4) *L. rhamnosus* ATCC53103 ("commercial" positive control)

The bacterial strains were cultured in Rogosa agar (*L. casei* and *L. paracasei*) and BHI Brain Heart Infusion (*Clostridium difficile*).

With the aim of verifying the ability of the strains of lactobacilli to exert an inhibitory action against CDIF.
Adhesion Test to Verify the Ability of Examples of Probiotics to Adhere to Intestinal Epithelial Cells As an example of a human intestinal epithelial cell line capable of producing mucus, use was made of HT29-MTX-E12 (ECACC). In particular, the cells were cultured until forming confluent monolayers in DMEM (Dulbecco's Modified Eagle Medium) with a high glucose concentration. The DMEM was supplemented with 10% fetal bovine serum with 50 µg/ml of gentamicin sulfate and 2 mM of L-glutamine. The cells were maintained in an incubator with 5% $CO_2$ at 37° C.

Prior to the adhesion test, the cells were washed with Hank's Balanced Salt Solution, trypsinized, resuspended, and counted by means of a single-use hemocytometer so that they could be seeded in multiwell plates at a known concentration. Before the adhesion test was carried out, the cells were made to grow for 2 days so as to form a confluent monolayer.

On the day of the adhesion test, the spent medium was removed, the monolayer was washed with the saline solution (Hank's Balanced Salt Solution) and the DMEM medium, without antibiotics or glutamine but supplemented with 1% fetal bovine serum, was added to the cells. The cell monolayer was incubated for 1 h at 37° C. with 5% $CO_2$ before being placed in contact with the bacteria. This operation removes any antibiotic residues that might interfere with the test.

The cells were subsequently "infected", observing an MOI (Multiplicity of Infection) of 1:10 (cells:bacteria).

Forty-eight hours after reaching confluence, the cells were washed and incubated with DMEM medium containing the example bacterial strains (single strains or strains in combination as described above) at a multiplicity of infection of 1:10 (MOI, epithelial cells:bacterium).

The incubation was carried out for 60 minutes at 37° C. with a slight oscillation of the plate to favor contact with the cells.

At the end of incubation, the culture medium was discarded, the cells were washed with sterile DMEM to remove non-adherent bacteria and the adherent bacterial cells were quantified by means of a viable microbial count using serial dilutions seeded on plates with agarized MRS medium incubated at 37° C. under anaerobiosis.

Adhesion Exclusion Test (Exclusion/Pre-Incubation)

After the number of HT29 cells per well had been determined, the strains of *L. paracasei* were added both individually and in combination in a 1:1 ratio (the mixture).

The bacteria were left in contact with the cells maintained at 37° C. with slight oscillation for 60 min.

At the end of the incubation, the medium was removed and the cells were washed with sterile medium to remove the bacteria that had not adhered to the monolayer.

COIF (MOI 1:10) was then added to the monolayer and the cells were incubated for 60 min at 37° C.

At the end of incubation, the culture medium was removed and the non-adherent bacteria were removed by washing with sterile medium.

In order to quantify the COIF adherent to the HT29 cells, the cells were first detached and then lysed and the bacteria were quantified by means of a viable bacterial count after seeding on *Clostridium difficile* Selective Agar under anaerobiosis for 48-72 hours at 37° C.

HT29 cells that had not been pre-incubated with the strains of *L. paracasei* but rather inoculated with COIF alone were used as a positive control, whereas the cells not incubated with any bacterium were used as a negative control (sterility test).

Competition for Adhesion Test (Competition Co-Incubation)

After the number of HT29-MTX cells per well had been determined, the two strains of *L. paracasei* (both individually and in combination in a 1:1 ratio) were added simultaneously with COIF.

The bacteria were added at an overall MOI of 1:10 and in a probiotic:pathogen ratio of 1:1. The bacteria were left in contact with the cells maintained at 37° C. with slight oscillation for 60 min.

At the end of incubation, the medium was removed and the cells were washed with sterile medium to remove the bacteria that had not adhered to the monolayer.

In order to quantify the CDIF adherent to the HT29 cells, the cells were first detached and then lysed and the bacteria were quantified by means of a viable bacterial count after seeding on *Clostridium difficile* Selective Agar under anaerobiosis for 48-72 hours at 37° C.

The HT29 cells inoculated with CDIF alone were used as a positive control, whereas the cells not incubated with any bacterium were used as a negative control (sterility test).

Test on Removal of Adherent Pathogens (Displacement/Post-Incubation)

After the number of HT29-MTX cells per well had been determined, the CDIF was added (MOI 1:10). The bacteria were left in contact with the cells maintained at 37° C. with slight oscillation for 60 min.

At the end of incubation, the medium was removed and the bacteria that had not adhered to the monolayer were removed by repeated washings with sterile medium. Then the two strains of *L. paracasei* (both individually and in combination in a 1:1 ratio) were added in a probiotic:adherent pathogen ratio of 10:1.

The bacteria were left in contact with the cells maintained at 37° C. with slight oscillation for 60 min. At the end of incubation, the medium was removed and the cells were washed with sterile medium to remove the bacteria that had not adhered to the monolayer.

In order to quantify the CDIF adherent to the cells, the cells were first detached and then lysed and the bacteria were quantified by means of a viable bacterial count after seeding on *Clostridium difficile* Selective Agar under anaerobiosis for 48-72 hours at 37° C.

The HT29-MTX cells inoculated with CDIF alone were used as a positive control, whereas the cells not incubated with any bacterium were used as a negative control (sterility test).

Results

Figure 1:
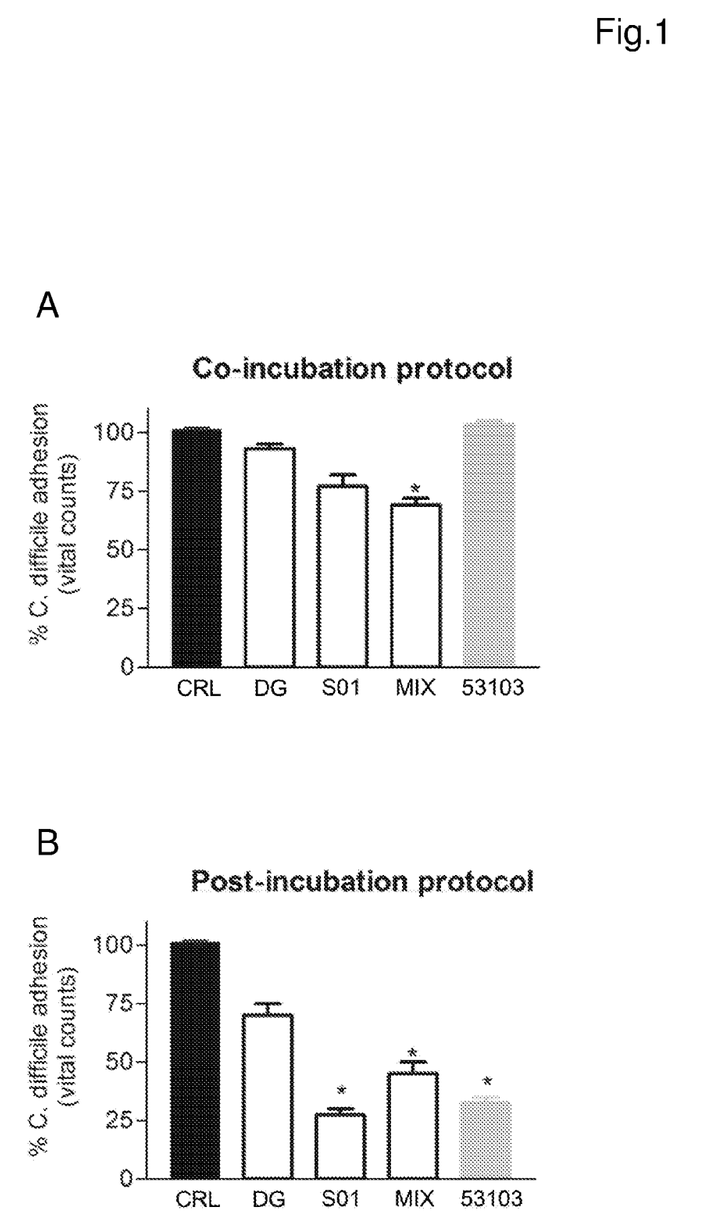
FIG. 1A shows the results of the competition for adhesion tests, i.e. the co-incubation of eukaryotic cells with the probiotics and with the pathogen. More specifically, the figure graphically represents CDIF adhesion in terms of percentage of adherent live and viable cells following co-incubation of HT29 cells with CDIF and with the various probiotics tested.
FIG. 1B shows the results of the tests on the removal of adherent pathogens, i.e. pre-treatment of the eukaryotic cells with the pathogen and subsequent incubation with the probiotic. More specifically, the figure graphically represents CDIF adhesion in terms of percentage of adherent live and viable cells following incubation of HT29 cells with the different probiotics tested, after the challenge of eukaryotic cells with CDIF.

The results are summarized in FIGS. 1A and 1B and demonstrate that:

1) the strain *L. casei* DG® showed a modest ability to directly reduce the adhesion of CDIF by about 7% compared to the condition of incubation of the cells with the pathogen alone, whereas the strain *L. paracasei* LPC-S01 showed greater effectiveness in competitively excluding CDIF (22% reduction in adhesion). The mixture of strains proved to be able to strengthen the inhibiting capacity, bringing about a 31% reduction in the adhesion of CDIF (FIG. 1A).

2) the strain *L. casei* DG® showed (FIG. 1B) a moderate ability to reduce the adhesion of CDIF by about 27% compared to the condition of incubation of the cells with the pathogen alone, whereas the strain *L. paracasei* LPC-S01 showed a significant effectiveness of "removal" of CDIF (75% reduction of adhesion).

EXAMPLE 2

The example strains were compared with a commercial product intended for the same purpose.

The pathogen used is the same strain as was used in the previous example.

The product Bio-K+ comprises a mixture of: *Lactobacillus acidophilus* CL1285, *L. casei* LBC80R and *L. rhamnosus* CLR2 at a declared concentration of 50 billion CFU per 98 g bottle, hence a declared concentration of $5.0 \times 10^{10}$ CFU/98 g ($5.1 \times 10^8$ CFU/g).

The product was subjected to a decimal count in a selective medium (ISTISAN method 08/36) in order to quantify the real total lactobacilli concentration. The concentration of live and viable cells was $1.2 \times 10^9$ CFU/g, thus about double the calculated theoretical concentration.

Adhesion Exclusion Test (Exclusion/Pre-Incubation)

After the number of HT29 cells per well had been determined, the product was added to the monolayer according to a pathogen/probiotic MOI of 1:10. The bacteria were left in contact with the cells maintained at 37° C. with slight oscillation for 60 min. At the end of incubation, the medium was removed and the cells were washed with sterile medium to remove the bacteria that had not adhered to the monolayer. CDIF was then added to the monolayer (MOI:1:10) and the cells were left to incubate for 60 min at 37° C.

At the end of incubation, the culture medium was removed and the non-adherent bacteria were removed by washing with sterile medium. In order to quantify the CDIF adherent to the HT29 cells, the cells were detached and lysed and the bacteria were quantified by means of a viable bacterial count after seeding on *Clostridium difficile* Selective Agar under anaerobiosis for 48-72 hours at 37° C.

Wells of HT29 cells not pre-incubated with the product, but inoculated with CDIF alone were used as a positive control, whereas wells of cells not incubated with any bacterium were used as a negative control (sterility test).

Competition for Adhesion Test (Competition/Co-Incubation)

After the number of HT29-MTX cells per well was determined, the product was added simultaneously with CDIF. The bacteria were added according to an overall MOI of 1:10. The bacteria were left in contact with the cells maintained at 37° C. with slight oscillation for 60 min. At the end of incubation, the medium was removed and the cells were washed with sterile medium to remove the bacteria that had not adhered to the monolayer. In order to quantify the CDIF adhering to the cells, the cells were detached and lysed and the bacteria quantified by means of a viable bacterial count after seeding on *Clostridium difficile* Selective Agar under anaerobiosis for 48-72 hours at 37° C. Wells of HT29 cells inoculated with CDIF alone were used as a positive control, whereas wells of cells not incubated with any bacterium were used as a negative control (sterility test).

Test on Removal of Adherent Pathogens (Displacement/Post-Incubation)

After the number of HT29-MTX cells per well had been determined, the CDIF was added (MOI 1:10). The bacteria were left in contact with the cells maintained at 37° C. with slight oscillation for 60 min.

At the end of incubation, the medium was removed and the bacteria that had not adhered to the monolayer were removed by repeated washings with sterile medium. Then the product was added in a 10:1 ratio of bacteria/cells as usual. The bacteria were left in contact with the cells maintained at 37° C. with slight oscillation for 60 min. At the end of incubation, the medium was removed, and the cells were washed with sterile medium to remove the bacteria that had not adhered to the monolayer. In order to quantify the CDIF adherent to the cells, the cells were detached and lysed and the bacteria were quantified by means of a viable bacterial count after seeding on *Clostridium difficile* Selective Agar under anaerobiosis for 48-72 hours at 37°. Wells of HT29-MTX cells inoculated with CDIF alone were used as a positive control, whereas wells of cells not incubated with any bacterium were used as a negative control (sterility test).

Results

Figure 2:
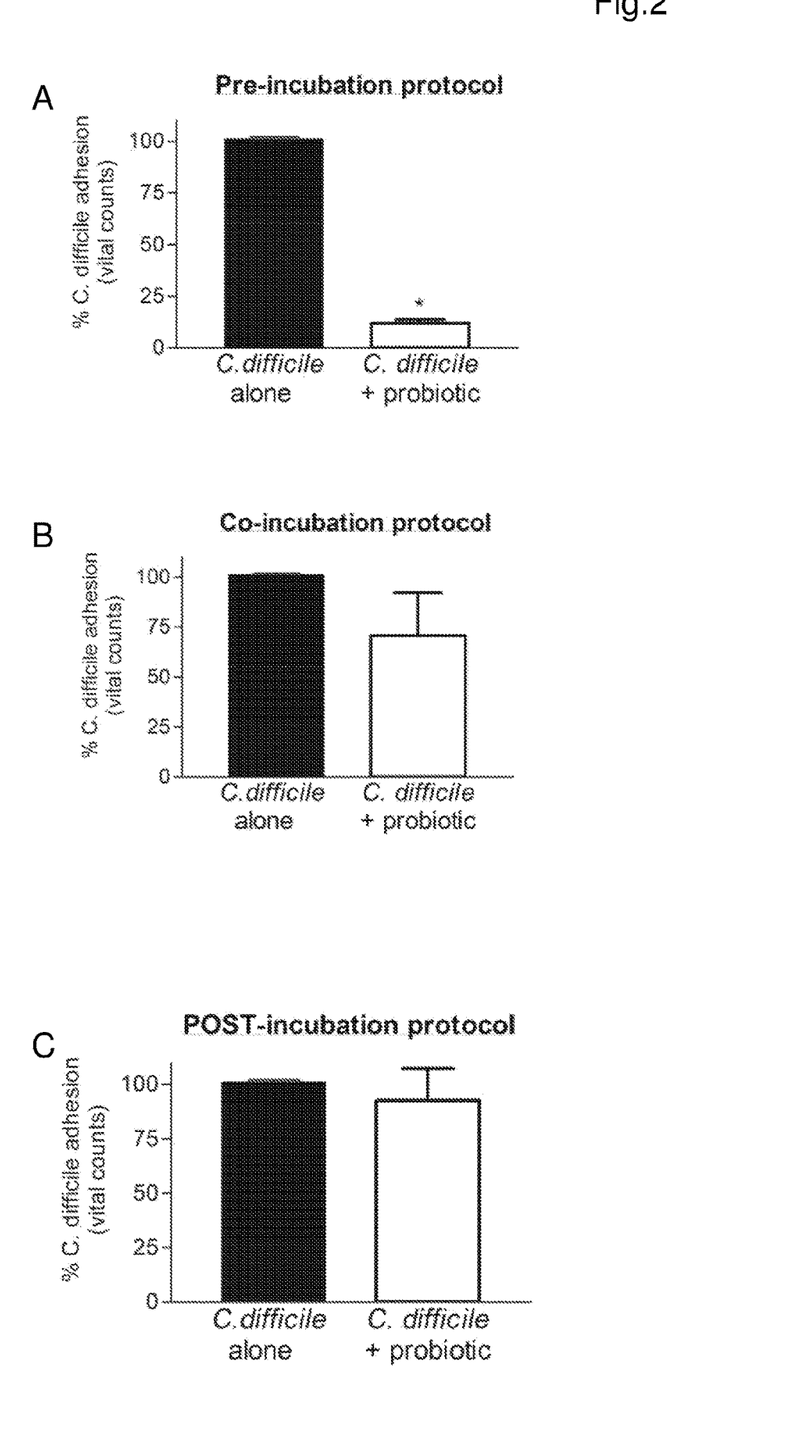
FIG. 2A shows the results of the adhesion exclusion tests (pre-treatment of the eukaryotic cells with the probiotic BIOK+ and subsequent incubation with the pathogen). More specifically, the figure graphically represents CDIF adhesion in terms of percentage of adherent live and viable cells following pre-stimulation by contact of HT29-MTX cells with the tested probiotic product Bio-K+.
FIG. 2B shows the results of the competition for adhesion tests (co-incubation of the eukaryotic cells with the probiotic and with the pathogen). More specifically, the figure graphically represents CDIF adhesion in terms of percentage of adherent live and viable cells following co-incubation of HT29-MTX cells with CDIF and with the tested probiotic product Bio-K+.
FIG. 2C shows the results of the tests on the removal of adherent pathogens (pre-treatment of the eukaryotic cells with the pathogen and subsequent incubation with the probiotic). More specifically, the figure graphically represents CDIF adhesion in terms of percentage of adherent live and viable cells following incubation of HT29 cells with the different probiotics tested, after the challenge of eukaryotic cells with CDIF.
Figure 3:
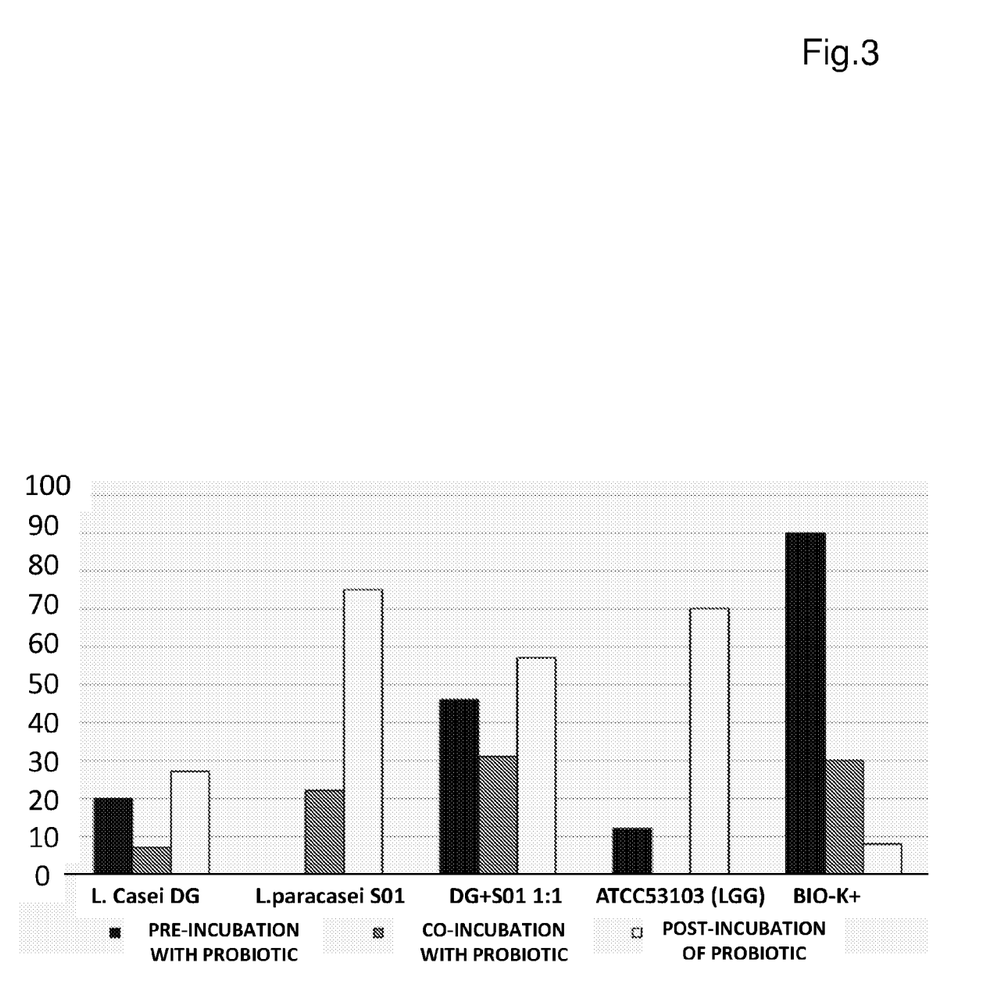
FIG. 3 shows the results of comparative analysis between the results of the tests performed with specific examples of probiotics compared to a commercial product known as Bio-K+, indicated against *Clostridium difficile* infection.

The results shown in FIG. 2A regard the adhesion of CDIF in terms of percentage of live and viable cells adhering after pre-stimulation by contact of the HT29-MTX cells with the tested probiotic product. In other words, where CDIF adhesion in the absence of stimulation by probiotics is assigned a value of 100, the inhibition capacity of the tested strains was expressed as a % reduction in CDIF adhesion compared to the positive control.

As may be noted, the tested product showed to be capable of reinforcing the inhibiting capacity, thus bringing about a very high reduction in CDIF adhesion, equal to 90%.

Moreover, the possible reduction in CDIF adhesion to HT29-MTX cells following a simultaneous treatment of the cell line with the probiotics and the pathogen was verified in order to assess the effect, if any, of the competitive inhibition exerted by the probiotics when co-incubated with CDIF.

Wells of HT29 cells inoculated with CDIF alone were used as a positive control, whereas wells of cells not incubated with any bacterium were used as a negative control (sterility test).

The results shown in FIG. 2B regard CDIF adhesion in terms of percentage of adherent live and viable cells following the co-incubation of HT29-MTX cells with CDIF and with the different probiotics tested. As described previously, where CDIF adhesion in the absence of stimulation by probiotics is assigned a value of 100, the inhibition capacity of the tested strains has been expressed as a % reduction in CDIF adhesion compared to the positive control.

As may be noted, the tested product showed to be capable of reinforcing the inhibiting capacity, thus bringing about a 30% reduction in CDIF adhesion.

Finally, it was verified whether there was any reduction in CDIF adhesion to HT29-MTX cells following pre-treatment of the cell line with the pathogen and subsequent incubation with the probiotics after removal of the non-adherent pathogen.

Wells of HT29 cells inoculated with CDIF alone were used as a positive control, whereas wells of cells not incubated with any bacterium were used as a negative control (sterility test).

The results shown in FIG. 2C regard CDIF adhesion in terms of percentage of adherent live and viable cells following incubation of the HT29 cells with the various probiotics tested, after the challenge of the eukaryotic cells with CDIF. As previously described, where CDIF adhesion in the absence of probiotics is assigned a value of 100, the inhibition capacity of the tested strains has been expressed as a % reduction in CDIF adhesion compared to the positive control.

As may be noted, the product showed a very modest inhibiting capacity, bringing about an 8% reduction in CDIF adhesion.

The table below summarizes the CDIF count ranges obtained in 2 successive tests compared to an initial pathogen load of about $1.0 \times 10^6$ CFU, for the 3 different protocols tested.

| Bio-k+ inhibitory activity | Range of 3 tests |
| --- | --- |
| C. difficile alone | $1.0 \times 10^3$-$1.4 \times 10^3$ |
| Co-incubation protocol | $5.1 \times 10^2$-$9.0 \times 10^2$ |
| Pre-incubation protocol | $1.0 \times 10^2$-$1.4 \times 10^2$ |
| Post-incubation protocol | $8.0 \times 10^2$-$1.1 \times 10^3$ |

Comparing the data obtained during the present study with those relating to the strains *L. casei* DG®, *L. paracasei* LPC-S01 and the mixture of the 2 strains, which were the subject of previous investigations, it was possible to draw up the profile shown below:

Adhesion Exclusion Test (Pre-Treatment of Eukaryotic Cells with the Probiotics and Subsequent Incubation with the Pathogen)

| Bacterial strain/product | % reduction in CDIF adhesion |
| --- | --- |
| *L. casei* DG | 20 |
| *L. paracasei* S01 | 0 |
| Mixture of DG + S01 1:1 | 46 |
| Bio-K+ | 90 |
| *L. rhamnosus* ATCC 53103 | 12 |

Competition for Adhesion Test (Co-Incubation of Eukaryotic Cells with the Probiotics and with the Pathogen)

| Bacterial strain/product | % reduction in CDIF adhesion |
| --- | --- |
| *L. casei* DG | 7 |
| *L. paracasei* S01 | 22 |
| Mixture of DG + S01 1:1 | 31 |
| Bio-K+ | 30 |
| *L. rhamnosus* ATCC 53103 | 0 |

Removal of Adherent Pathogens Rest (Pre-Treatment of the Eukaryotic Cells with the Pathogen and Subsequent Incubation with the Probiotic)

| Bacterial strain/product | % reduction in CDIF adhesion |
|---|---|
| L. casei DG | 27 |
| L. paracasei S01 | 75 |
| Mixture of DG + S01 1:1 | 57 |
| Bio-K+ | 8 |
| L. rhamnosus ATCC 53103 | 70 |

The overall results shown in the 3 tables demonstrate that:

1) the strain L. paracasei LPC-S01 is the most effective; in particular, during the displacement tests it showed a very high inhibition capacity against CDIF (75%). In other words, the strain L. paracasei LPC-S01 acts after the adhesion of the pathogen and removes it, unlike the tested commercial product, which performs only a preventive function, as it prevents the pathogen CD from adhering to cells; in this case, the tested strain L. paracasei LPC-S01 also works when the pathogen CD is already adherent; and 2) the 1:1 combination of L. casei DG®+L. paracasei LPC-S01 showed an interesting synergistic effect with respect to the reduction in the adhesive capacity of CDIF vis-á-vis the cell line. The combination revealed to be advantageous compared to the individual strains in the pre-treatment and co-incubation protocols, whereas in the displacement tests the strain L. paracasei LPC-S01 proved to be more effective than the combination of the 2 probiotics.

The invention claimed is:

1. A composition comprising:
   a therapeutically acceptable amount of a combination of Lactobacillus paracasei CNCM I-1572 and Lactobacillus paracasei LPC-S01; and
   a pharmaceutically acceptable excipient.

2. The bacterial composition according to claim 1, wherein said composition further comprises micro-organisms chosen from the group consisting of: probiotic bacteria, yeasts and fungi.

3. The composition of claim 2, wherein the probiotic bacteria belongs to a genus selected from: Lactobacillus, Bifidobacterium, Bacillus, Propionibacterium, Streptococcus, Lactococcus, Aerococcus, Enterococcus and combinations thereof, and wherein said probiotic bacteria belong to the genus Lactobacillus e/o Bifidobacterium.

4. The bacterial composition according to claim 1, wherein said therapeutically effective amount is in the range of 1 billion to 300 billion cells for each bacteria.

5. The bacterial composition according to claim 1, wherein the composition is formulated as a pill, capsule, tablet, granular powder, soluble granules, sachets, sugar coated pill; or in liquid form, a syrup or drink; or added to a food, yoghurt, cheese or fruit juice as an additive.

6. The bacterial composition according to claim 1, wherein the composition is formulated for rectal administration.

7. A method of treating a Clostridium difficile infection, comprising: administering a therapeutic amount of a composition comprising a combination Lactobacillus paracasei CNCM I-1572 and Lactobacillus paracasei LPC-S01 to a patient infected with Clostridium difficile.

8. The method of claim 7, wherein the patient has an intestinal Clostridium difficile infection.

9. The method of claim 7, wherein the patient has pseudomembranous enterocolitis, pseudomembranous colitis, pseudomembranous colitis without pseudomembranes, fulminant colitis, colitis with toxic megacolon and intestinal perforation, colitis associated with antibiotics, diarrhea associated with antibiotics, diarrhea associated with C. difficile infection.

10. The method of claim 7, wherein the patients has one or more of the following symptoms: diarrhea, dehydration, pseudomembranous colitis, enteropathies, toxic megacolon, intestinal perforation, sepsis, intestinal haemorrhaging and hypokaliemia.

11. The method of claim 7, wherein the composition further comprises a probiotic bacteria, and/or yeasts and/or fungi.

12. The method of claim 11, wherein the composition further comprises the probiotic bacteria belonging to a genus selected from: Lactobacillus, Bifidobacterium, Bacillus, Propionibacterium, Streptococcus, Lactococcus, Aerococcus, Enterococcus and combinations thereof.

13. The method of claim 7, wherein the therapeutically effective quantity varies from 1 billion to 300 billion or more, as appropriate for each intake.

14. The method of claim 7, wherein the composition is administered at least one-twice daily.

15. The method of claim 7, wherein the composition is administered orally.

16. The method of claim 7, wherein the composition is administered rectally.

* * * * *